United States Patent [19]
Wickham

[11] 3,972,334
[45] Aug. 3, 1976

[54] DEMAND HEART PACER WITH DUAL TIME BASES

[75] Inventor: Geoffrey Gordon Wickham, Longueville, Australia

[73] Assignee: Telectronics Pty. Limited, Australia

[22] Filed: Feb. 10, 1975

[21] Appl. No.: 548,244

[52] U.S. Cl. ........................................ 128/419 PG
[51] Int. Cl.² ........................................... A61N 1/36
[58] Field of Search..... 128/419 P, 419 PG, 419 PS, 128/419 PT, 419 R, 421, 422, 423, 2.06 F, 2.06 R

[56] References Cited
UNITED STATES PATENTS

| | | | |
|---|---|---|---|
| 3,518,997 | 7/1970 | Sessions | 128/419 PG |
| 3,656,487 | 4/1972 | Gobeli | 128/419 PG |
| 3,662,759 | 5/1972 | Dabolt | 128/419 PG |
| 3,718,909 | 2/1973 | Greatbatch | 128/419 PT |
| 3,782,367 | 1/1974 | Hochberg et al. | 128/419 PT |
| 3,870,050 | 3/1975 | Greatbatch | 128/419 PG |

Primary Examiner—William E. Kamm
Attorney, Agent, or Firm—Flehr, Hohbach, Test, Albritton & Herbert

[57] ABSTRACT

A heart pacer providing heart stimulating electrical impulses in the absence of naturally occurring heartbeats, including two electrical impulse generating time bases each capable of emitting heartbeat stimulating impulses. A sensed signal, accepted against criteria preceding it in time, as a valid heartbeat signal rather than an interference signal, serves to reset one time base while a second time base continues its cycle on the assumption that the sensed signal is an invalid or interference signal. If further signals are sensed, within criteria indicating that the original sensed signal was, in fact, invalid, the second time base continues its cycle until it emits a heart stimulating impulse at which time the first time base timing cycle is cancelled. If, however, the original sensed signal is not shown to be invalid the output of the second time base is suppressed and the reset timing cycle of the first time base continues. The pacer allows the validity of the sensed signal to be judged against both preceding and succeeding criteria.

16 Claims, 4 Drawing Figures

DEMAND HEART PACER WITH DUAL TIME BASES

BACKGROUND OF THE INVENTION

The invention relates to demand cardiac pacers and particularly to a pacer in which the probability of inhibition of one or more heart stimulating impulses by interfering electrical signals is substantially reduced whether those interfering signals are physiological or non-physiological in origin.

The term "demand pacer" describes that particular type of pacer in which an electrical impulse generator is connected by wires and electrodes to the heart of the patient such as to deliver pulses of a heart stimulating magnitude at a rate approximately of a normal heart beating rate. In addition, the demand pacer includes an electrical amplifier connected also to the heart and having its parameters such that it is sensitive to the electrical manifestations of a heartbeat. Upon sensing a heartbeat by the amplifier further circuitry is activated to produce a triggering impulse which is delivered to the pacing pulse generator circuit to reset the timing cycle of the pulse generator and to inhibit the generation of the next otherwise delivered heart stimulating impulse. Such a pacer is described in U.S. Pat. No. 3,345,990, issued Oct. 10, 1967 to B. V. Berkovits for "Heart-Beat Pacing Apparatus".

In another form of the demand pacer, originated by applicant and incorporated in commercial designs since 1970, the action of resetting the pacing pulse generator upon detection of a natural heartbeat is accompanied by delivery to the heart electrodes of a pulse of less than heartbeat stimulating magnitude. This variant allows the cardiologist to recognize normal pacer sensing actions in the presence of continuous natural heartbeats.

Both of these variations come within the definition of a "demand pacer," to which the present invention relates. In the demand pacer of either of these types, because a sensed signal produces resetting of the pacing pulse generator without delivery of an impulse of heart stimulating magnitude to the heart, the sensing of electrical interfering signals can cause complete suppression of the pacing function in the absence of natural heart rhythm — a life threatening situation. Thus, it can be seen that it is essential to minimize or eliminate the probability that any given interfering electrical signal might cause maloperation of a demand pacer.

The principal, but not sole, objective of the present invention is to reduce the probability of demand pacer response to interfering electrical signals. To this same end, prior art pacers have provided for tuning the demand sensing amplifier such as to make it most sensitive to those frequencies contained within that electrical manifestation of a naturally occurring depolarization of the cardiac muscle cells commonly described in clinical practice as the QRS sector of a cardiogram. Conversely, it is tuned to be less sensitive or insensitive to frequencies outside the QRS spectrum. The spectrum lies between approximately 20 Hz. and 100 Hz. with the frequency of peak energy density varying considerably from subject to subject.

With such tuning it is, of course, possible to eliminate the effect of interfering signals having frequencies outside the spectrum if of moderate magnitude. However, interfering signals can be of a magnitude many times greater than the heart's QRS signal and thus penetrate the tuning of the sensitive amplifier even when not containing frequencies within the amplifier's tuned spectrum.

Additionally, common sources of electrical interference produce frequencies within the amplifier's tuned spectrum. Included among these are sources of 50 Hz. to 60 Hz. power mains, arc producing devices, such as welders or commutator machines, and other muscles of the body. Additionally, the interfering signals may not be a continuous wave of one discrete frequency but may contain many frequencies or be comprised of periodic or non-periodic short bursts of interference. As stated earlier, suppression of the heartbeat pacing impulses of a demand pacer by interfering signals is a life threatening event where the patient's heart is not beating in a natural rhythm at the time. In contrast, it is generally agreed that a situation in which the pacer delivers heart stimulating impulses at its preset rate even in the presence of naturally occurring heartbeats, can be tolerated by most patients for short periods.

There has been provided in the prior art designs such that the heart pacing impulses of the demand pacer are not suppressed but continue to be delivered at the preset rate even in the presence of certain forms of interference. Should the patient, at that time, have a natural heart rhythm, there will occur competition between the natural heart rhythm and the pacer stimulating rhythm. However, as previously stated, this is tolerable in a short term and unquestionably preferable to the life threatening alternative.

Examples of such prior art are two U.S. Pat. in the name of B. V. Berkovits, Nos. 3,528,428, issued Sept. 15, 1970 for "Demand Pacer" and 3,766,413, issued Oct. 15, 1973 for "Rate Discrimination Circuit". In these patents a demand pacer is described which, when sensing continuous wave electrical interference signals having a repetition rate much greater than a natural hearbeat repetition rate (for instance, 50 Hz. to 60 Hz. line interference) delivers heart stimulating impulses at its preset rate rather than having its heart stimulating impulses suppressed. In such a pacer the sensed signals are fed, after amplification, to a pulse forming circuit and then to a circuit having a resistive-capacitive (R-C) time constant.

When the time interval between two successive input events is similar to, or larger than, the R-C time constant, a large voltage change occurs across the capacitor and it is this large voltage excursion which triggers or resets the pacer pulse generator timing circuit. Where the interval between two successive events is small compared to the R-C time constant, there is little change in the voltage across the capacitor at the occurrence of the second event and too little to trigger or reset the pacer timing circuit. This principle is most effective in preventing dangerous pacer operation in the presence of continuous wave electrical interference. However, the leading edge of the interference can trigger or reset the pacer pulse generator timing circuit once. Thus, if the interfering signal is in the form of short bursts, or is modulated or otherwise fluctuating in magnitude or frequency content, and the rate of the burst or modulation or fluctuation is not short compared to the R-C time constant, then the pacer output can be held suppressed for as long as the interference persists.

A further example of the prior art is a demand pacer which is refractory, that is, inoperative, for the first three-eights of the pacer pulse generator timing cycle as measured from the last sensed event or delivered heart stimulating impulse. This device is set forth in a Cordis Corporation manual entitled Omni-Stanicor Implantable R-Wave Inhibited Cardiac Pacer in the Programmable Omnicor System, dated November 1972 and specifically pages 11-4 and 11-12 thereof. In this example, at the end of the refractory period is an interference sampling period having the duration of one-sixteenth of the pacer pulse generator timing cycle. During the interference sampling period any input events (voltage fluctuations crossing zero) are counted and, if exceeding a predetermined number (four), the input is classified as interference. The circuitry then, normally active to reset the pacer pulse generator timing cycle is deactivated for the remainder of the timing cycle and the heart stimulating impulse is delivered and the cycle recommenced. The effectiveness of this principle is limited in that interference can only be discriminated against by being detected during the short interference sampling period.

Moreover, four or fewer pulses during the sampling period will not be recognized as interference while a pulse or burst outside the narrow sampling period will falsely reset the pulse generator. In other words, the principle is most effective in the presence of continuous wave interference, and only effective in the case of bursts of interference if the bursts coincide with the short interference sampling period.

SUMMARY OF THE INVENTION AND OBJECTS

A principal objective of the present invention is to reduce the probability of demand pacer response to interfering electrical signals; that is, any signal of sufficient magnitude to be sensed by the amplifier of the demand pacer and originating from any source other than the naturally occurring depolarization of the cardiac muscle cells as evidenced cardiographically by that electrical manifestation known in medical practice as the QRS sector of the cardiogram.

The pacer of the present invention includes means by which the validity of a sensed signal may be judged against any given criteria, not only in the time period preceding the sensed signal, but also for an extended period after the sensing of the signal. All this is done without delaying the instant of reset of the pulse generator timing cycle relative to the instant of sensing a signal.

More specifically, the pacer includes terminal means for connection to a patient, together with means to generate heart stimulating electrical impulses for application to the terminal means. The electrical impulse generating means includes first and second electrical timing means having first and second predetermined timing periods. The electrical impulse generating means also includes means for selecting either the first or the second electrical impulse timing means in response to criteria which is predetermined as compared with a sensed signal.

DETAILED DESCRIPTION OF THE PREFERRED EMBODIMENT

Applicant's investigation and analysis of the characteristics of sensed heartbeat signals, of interfering signals and of demand pacer behavior have led to certain conclusions which form the basis of the signal evaluation circuit of the present invention. First, the time duration of certain electrical manifestation of a single heartbeat, that is, the QRS of the endocardiogram, never exceeds a certain time period. Secondly, an arbitrary lower limit to the time interval between two natural heartbeats may be assigned. Although somewhat subjective, a normal rate for the heart may be assumed at about 70 beats per minute or about 860 milliseconds between pulses. The arbitrary lower limit lies between 30% and 40% of normality.

By combining these two observations, the criteria for providing a degree of discrimination between a sensed natural heartbeat and a sensed interference signal may be established. Any sensed signal occurring later than the first time period but prior to the end of the second time period, all measured from the immediately preceding sensed signal, is classified as interference.

The sensing of any single interference signal implies to a high degree of probability that a second interference signal will follow before the next natural heartbeat. Thus, upon sensing an interference signal, the means normally operative to reset the pacing pulse generator timing circuit should be disabled and held disabled at least until after delivery of the next heart stimulating impulse delivered by the pacer.

A time delay may be introduced, within physiologically dictated limits, between the instant of sensing a signal from the heart electrodes and the instant of resetting the pacing pulse generator timing cycle. The physiological limit arises because this resetting delay increases the time interval between a sensed heartbeat and a paced heartbeat by the amount of the delay. This constraint limits the period of delay to not greater than some 100 milliseconds for a pacer having a free running pace rate of seventy beats per minute.

This time delay is effective in enhancing interference discrimination in that it allows for some retrospective examination of the validity of any sensed signal.

In applicant's prior pending application, Ser. No. 540,973, filed Jan. 14, 1975, entitled "Demand Heart Pacer with Improved Interference Discrimination" there is described a pacer which functions in accord with a prestated interference discrimination criteria. In that pacer there is included means by which a short delay is introduced between the instant of sensing an input signal and the instant of resetting the pulse generator timing cycle. This, of course, allows the validity of the sensed signal to be examined against criteria during the immediately succeeding short period of delay. The period of delay is limited, by physiological dictates, to approximately 100 milliseconds and is thus of restricted effectiveness in that the time period during which interference testing criteria may be employed is short. Additionally, utilization of the delay requires that the time period between the sensed beat and a succeeding paced beat is greater (by the time period of the delay) than the period between two paced beats. This phenomenon known as "hysteresis" is not acceptable to all physicians.

Figure 1:
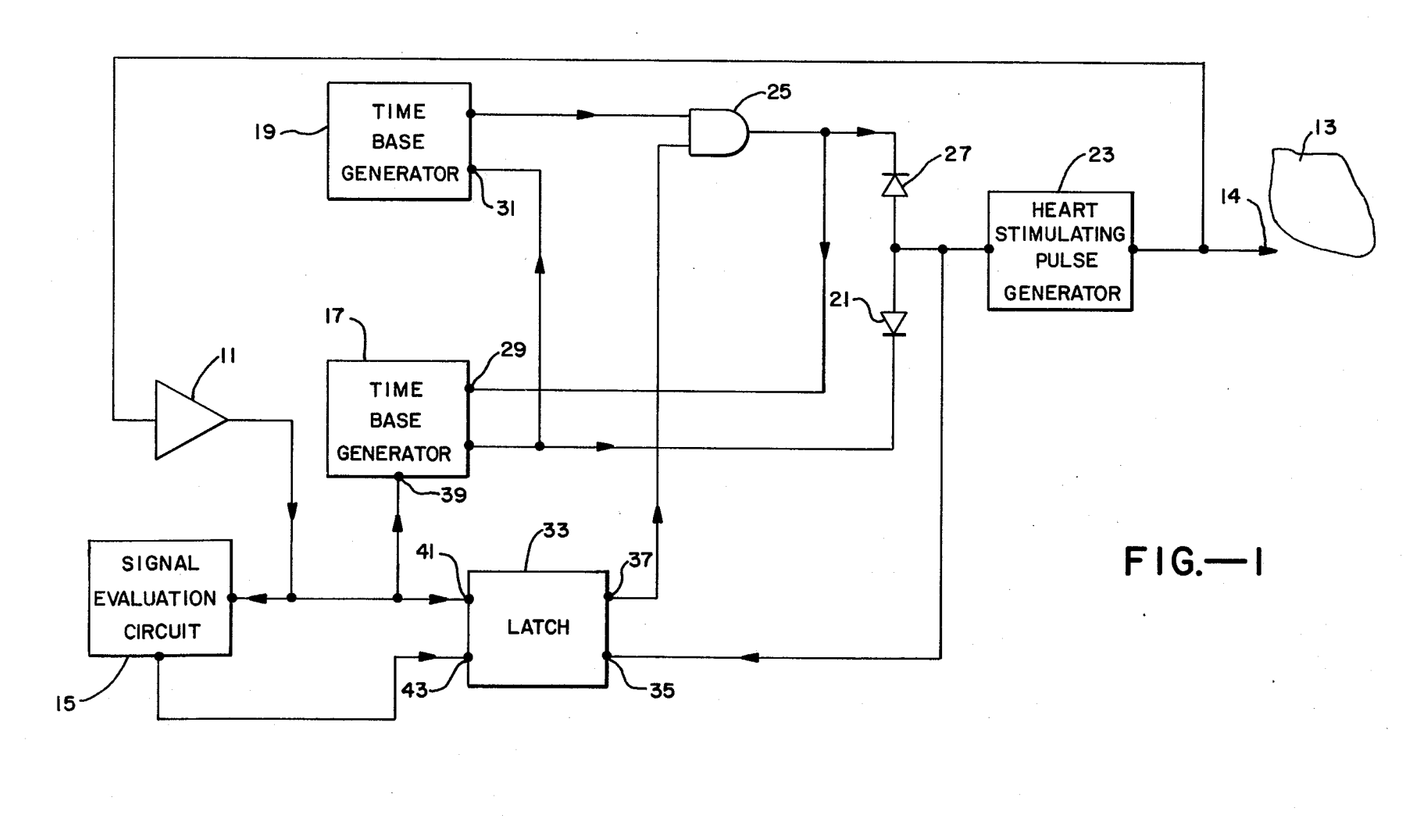
FIG. 1 is a block diagram showing a preferred embodiment of the invention.

Referring to FIG. 1, the invention is illustrated in block diagrammatic form. There, there is shown an amplifier 11 which senses low level signals from the heart 13 and generates "control" pulses coincident with the appearance at the terminal 14 connected to the heart, of signals above a predetermined voltage. This is a standard function well known to those experienced in the art. A signal evaluation circuit 15 tests the validity of the sensed signal or signals against predetermined criteria. The criteria employed may vary widely without effecting the essence of the present invention. The signal evaluation circuit 15 generates pulses at its output detection of an invalid signal. These pulses are nominated "invalidate" pulses.

Two time base generating circuits 17 and 19 are employed. The free running period of each time base generator is essentially the same and typically in the order of 820 to 860 milliseconds, that is, approximately 70 beats per minute. The output of time base generator 17 is coupled by a diode 21 to a heart stimulating pulse generator 23. At the termination of the timing period of the time base generator 17 a heart stimulating impulse is thus applied to the heart 13 through the terminal 14. Similarly, the output of the time base generator 19 is coupled by way of a gate 25 and diode 27 such that, with gate 25 enabled, the termination of the time period of time base generator 19 causes a heart stimulating impulse to be applied to the heart 13.

Both time bases have reset inputs 29 and 31, respectively. The termination of the time period of time base generator 17 always resets the time base generator 19 so that both begin a new timing period in synchronism. Similarly, when but only when, gate 25 is enabled, the termination of the timing period of time base generator 19 will reset the generator 17 so that both begin a new time period in synchronism.

A latch 33 is set by way of input 35 by any pulse at the junction of diodes 21 and 27, that is, whenever a pacing pulse is emitted. When latch 33 is set, its output at 37 directs that the gate 25 is enabled. A control pulse applied to the input 39 of the time base generator 17, resets that generator to begin a new timing cycle. Simultaneously, the control pulse is applied to the input 41 of latch 33 to unset the latch and disable gate 25. Any invalidate pulse applied to input 43 of the latch 33 resets the latch and again enables gate 25.

Thus, it is seen that, in the absence of any control pulses at the input 39 of time base generator 17 and the input 41 of latch 33, time base generators 17 and 19 will function in synchronism with simultaneous and mutual reset so as to provide heart stimulating impulses to the heart 13 at a predetermined pacing rate.

If a control pulse is applied to the input 39 of the time base generator 17 and the input 41 of the latch 33, the time base generator 17 will be reset to begin a new timing cycle and the gate 25 will be disabled. The time base generator 17, in the absence of further control pulses, will at the completion of its timing cycle cause a heart stimulating impulse to be provided to the heart 13. If, prior to the completion of the timing cycle of the generator 17, a further control pulse is applied to the input 39 of the generator 17 and the input 41 of the latch 33, then the time base generator 17 is further reset to begin a further timing cycle. At the expiration of the timing cycle of the generator 17, an output pulse from the generator 17 resets the timing cycle of the generator 19. At the same time a heart stimulating impulse is delivered to the heart 13 and the latch 33 is again reset through input 35 causing an output at its terminal 37 to reenable the gate 25.

If, after the timing cycle of the generator 17 has been reset by a control pulse, an invalidate pulse is received at the input 43 of latch 33, then the latch is reset and the gate 25 is reenabled. Time base generator 19 will thus, at the end of its timing cycle, cause a heart stimulating impulse to be delivered to the heart 13 with coincident resetting of the timing cycle of the generator 17 so that both generators 17 and 19 begin a new cycle in synchronism. Thus, a sensed signal may be tentatively accepted as valid and the time base generator 17 reset. However, later events may show the signal to be invalid, so time base generator 19 applies a pacing pulse to the heart at the end of its predetermined interval and the on going but invalid timing cycle of the generator 17 is cancelled.

In general then, the system provides for the use of two time bases responsive to pulses derived from a heartbeat sensing means. Each time base is capable of producing a heartbeat stimulating impulse at the end of its own predetermined time period. When a signal is sensed, one time base continues its preestablished timing cycle on the tentative assumption that the sensed event is not a valid heartbeat signal. The second time base, on the other hand, is reset in response to the sensed signal on the assumption that the sensed signal is a valid heartbeat signal. Either of the two tentative decisions may subsequently be cancelled.

Considerable variation of the interrelationship of the two time bases may be designed without departing from the essence of the invention. In the example of FIG. 1, as well as in the example to be described hereinafter, the two time bases are mutually reset, each beginning new timing cycles after the delivery of a heart stimulating impulse. However, the system may be designed such that in the absence of a control pulse only one time base generator is running to produce a heart stimulating impulse at the predetermined pacing interval. Upon receipt of a control pulse the dormant time base is then activated to commence its timing cycle.

Alternatively, the two time bases may in the absence of a control pulse run sequentially. That is, at the completion of the timing cycle of one, the second commences a timing cycle and the first lies dormant. Again, receipt of a control pulse activates the dormant time base to begin a new timing cycle.

Further, other variations will become known to those skilled in the art such as the use of a microcomputer and appropriate programming.

In the embodiment of FIG. 1, the control pulse applied to the latch 33 and to the time base generator 17 resets the generator 17 and disables gate 25 on the assumption that the sensed signal which caused the control pulse is a valid heartbeat signal. If further sensed signals indicate that the first sensed signal was invalid then an invalidate pulse is applied to the input 43 of the latch 33 thereby resetting the latch and reenabling gates 25 so the time base generator 19 will cause a heart stimulating impulse to be delivered at the end of its timing cycle. However, if still another tentatively valid signal is sensed prior to the expiration of the timing cycle of the generator 19 then the time base generator 17 will be again reset, the latch 33 again unset and the gate 25 again disabled. This allows an on going situation of acceptance or reversal of any tentative decision.

Figure 2:
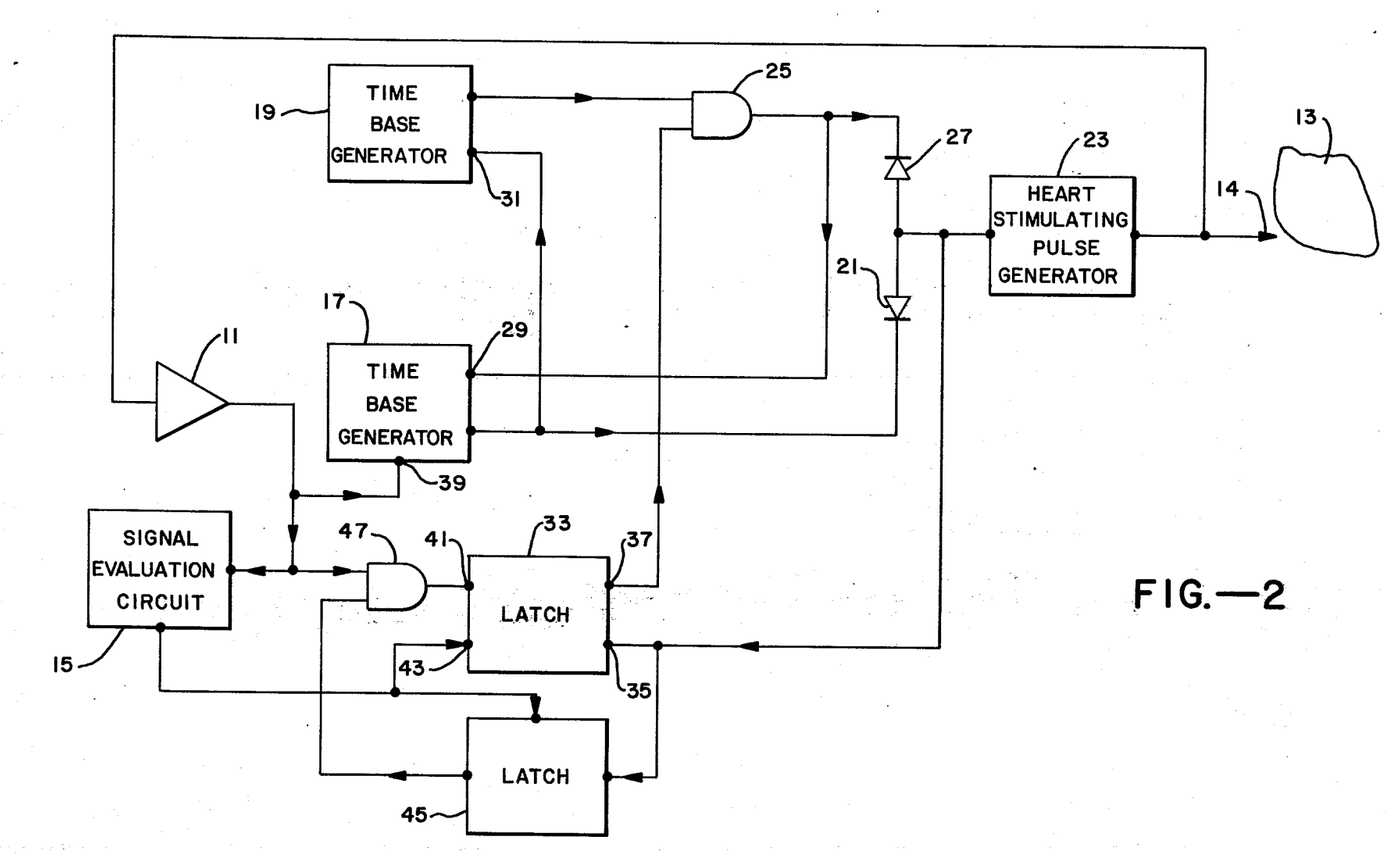
FIG. 2 is a block diagram showing an alternative embodiment of the invention.

Referring to FIG. 2, an alternative embodiment of the invention is shown wherein an additional latch is incorporated. For the most part the block diagram of FIG. 2 is identical to that of FIG. 1 and like parts carry the same reference numerals. The additional latch 45 in the embodiment of FIG. 2 has its output connected to a gate 47. When enabled, the gate 47 permits an output from the amplifier 11 to be passed to the input 41 of the latch 33. The latch 45 is set by any pacing pulse appearing at the junction of diodes 21 and 27 and when the latch is set it enables the gate 47. An invalidate pulse from the signal evaluation circuit 15, unsets the latch 33 by way of input 43, as in the prior described embodiment. Additionally, the invalidate pulse is applied to the latch 45 and unsets that latch. The gate 47 is thus disabled and held disabled until the latch 45 is again set by the next pacing pulse appearing at the junction of the diodes 21 and 27. Origination of this pacing pulse is time base generator 19, by way of gate 25 which is held enabled by the unset condition of the latch 33. This occurs even though a further tentatively valid control pulse may arrive prior to the terminaton of the timing cycle of the time base generator 19.

Whether the embodiment of FIG. 1 or FIG. 2 is chosen for a given pacer design depends essentially upon the sophistication and criteria employed in the signal evaluation circuit 15.

Figure 3:
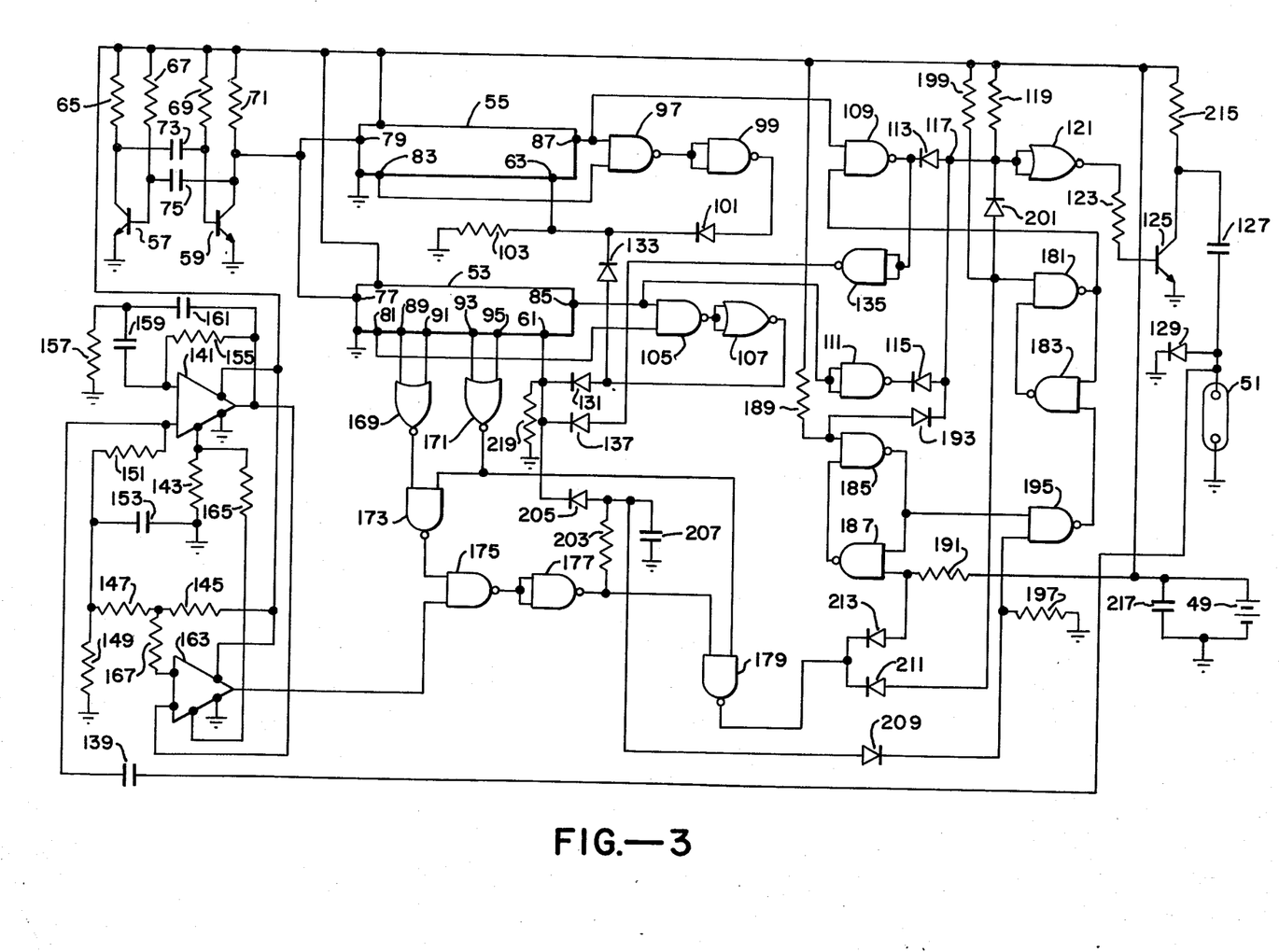
FIG. 3 is a schematic diagram showing the invention depicted in FIG. 2.

Referring to FIG. 3 there is shown a schematic diagram illustrative of the embodiment shown in block form in FIG. 2. In the actual circuitry of FIG. 3 all logic blocks utilize C-MOS technology so that battery current drain is equal to or less than that in simple conventional pacers. The battery 49 which is employed is nominally of 4.2 volts as may be derived from 3 mercury oxide-zinc cells. Terminals 51 are for connection to the heart electrodes. The time base generators comprise 11 bit binary counters or dividers 53 and 55 driven by multivibrator clock transistors 57 and 59, together with associated components. The binary counters each have common reset lines, terminals 61 and 63.

The primary timing mechanism is the multivibrator comprising transistors 57 and 59, together with resistors 65, 67, 69 and 71 and capacitors 73 and 75. The operating principle of the classic multivibrator is well known and needs no explanation. The values of timing capacitors 73 and 75 and their associated resistors 67 and 69 are chosen such that the generator pulses have a period of 800.78 microseconds. The clocking pulses are coupled from the collector of transistor 59 to the inputs 77 and 79 of binary counters 53 and 55. First output terminals 81 and 83 (count of 2) of the counters 53 and 55 undergo a change of state each 800.78 microseconds while final output terminals 85 and 87 (count of 2048) undergo a change of state after 820 milliseconds (800.78 microseconds × 1,024). Intermediate output terminals 89, 91, 93 and 95 (counts of 128, 256, 512 and 1024) of the counter 53 have, respectively, a change of state at 51.25 milliseconds (800.78 microseconds × 64), 102.5 milliseconds (800.78 microseconds × 128), 205 milliseconds (800.78 microseconds × 256), and 410 milliseconds (800.78 microseconds × 512).

The outputs 83 and 87 of the counter 55 are both coupled to a NAND gate 97. When the output 87 goes from logic level 0 to logic level 1 after 820 milliseconds, output 83 is at logic level 0 and goes to logic level 1 800.78 microseconds later. At that moment both inputs to NAND gate 97 are at logic level 1 so that its output goes from logic level 1 to logic level 0. This is inverted to logic level 1 by NAND gate 99 and applied to the reset terminal 63 through the diode 101. Terminal 63 is normally held at logic level 0 by connection to ground through resistor 103. The same sequence applies to counter 53 employing NAND gate 105 and NOR gate 107. All outputs of the counters 53 and 55 are thus set to logic level 0 at the beginning of each new count cycle. After 820 milliseconds from each reset instant, the outputs 85 and 87 rise from logic level 0 to logic level 1 for a duration of 800.78 microseconds.

The output 87 of the counter 55 is also fed as an input to NAND gate 109 whose other input is normally held at logic level 1, as will be seen hereinafter. During the 800.78 microseconds that gate 109 receives a logic level 1 output pulse from the terminal 87, a logic level 0 output pulse appears at the output of the gate 109. In the same manner the output from the terminal 85 of counter 53 is fed to an inverter 111 whose output is a logic level 0 pulse of 800.78 microsecond duration upon the occurrence of a pulse from the terminal 85. The output from the gates 109 and 111 are fed respectively through diodes 113 and 115 to a common point 117 normally held at logic level 1 by connection to the positive terminal of battery 49 through resistor 119. The common point 117 is applied as an input to the inverter 121 whose output thus goes from logic level 0 to logic level 1 for 800.78 microseconds. The output of the inverter 121 is fed through resistor 123 to the base of pacing output transistor 125. Thus the collector of the transistor 125, normally at logic level 1, goes to logic level 0 for the duration of each pulse from the inverter 121. When the collector of transistor 125 is at logic level 1, capacitor 127 charges by way of the terminals 51. When the collector of transistor 125 goes to logic level 0 with each pulse from the inverter 121, the capacitor 127 is discharged to provide a heart pacing pulse through the terminals 51 to the heart. The capacitor 127 ensures that there is no net charge applied to the heart electrodes, the charge applied during the active or pulse phase being equal to the charge extracted during the period between pulses. Diode 129 is provided as protection for the normally cathodic electrode or the terminal 51 which is, during the recovery phase, instantaneously anodic.

Referring again to the counters 53 and 55, it is seen that the output of the inverter 107 serves not only to reset its associated counter 53 by application of the pulse to the terminal 61 through the diode 131 but it also serves to reset the counter 55 by application of the pulse to the reset terminal 63 through the diode 133. Thus, any reset of the counter 53 produces a coincident reset of the counter 55. Similarly, the output pulse of the counter 55, appearing at the output of the gate 109 will reset the counter 53 by way of the inverter 135 and diode 137.

Thus, in the fixed rate pacing mode, that is with the gate 109 enabled, both counters run synchronously with mutual resetting and pacing pulses of 800.78 microsecond duration are applied to the heart each 820 milliseconds.

Sensed signals appearing at the terminals 51 are applied by way of capacitor 139 to the noninverting input of an amplifier 141. Amplifier 141 is a programmable monolithic operational amplifier whose working current level is set to approximately 3 microamperes by resistor 143. The DC working point is set by the resistive divider chain comprising resistors 145, 147 and 149 connected between ground and the positive terminal of battery 49. The junction of resistors 147 and 149 is applied through the resistor 151 also to the noninverting input of amplifier 141. Capacitor 153 acts as a bypass to the resistor 151 so that pacing pulses at the terminal 51 coupled by the capacitor 139 do not produce a disturbance of the divider voltages in the chain of resistors 145, 147 and 149.

Stabilizing DC feedback is applied from the output of the amplifier 141 by way of resistor 155 to the inverting input of the amplifier. The frequency response of the amplifier is optimized to the frequency of the QRS of a heartbeat by AC feedback provided by the resistor 157 and capacitors 159 and 161.

The output of amplifier 141 is directly coupled to the noninverting input of another amplifier 163. The amplifier 163 is an identical component to the amplifier 141 but is operated as an open loop comparator. The working current level of the amplifier 163 is set by a resistor 165, together with resistor 143. The inverting input of amplifier 163 is derived from the same resistive divider chain which sets the DC working point of amplifier 141, that is, resistors 145, 147 and 149. However, the junction feeding the inverting input of amplifier 163 is that of resistors 145 and 147 which is connected to the amplifier 163 through the resistor 167. The junction of the resistors 145 and 147 is 105 millivolts higher than is the junction of the resistors 147 and 149. Thus, the output of amplifier 163 is normally at logic level 0 switching to logic level 1 when a signal is sensed by the amplifier 141 of sufficient magnitude to cause its output to rise from its DC working level by greater than 105 millivolts. This pulse, or pulses, at the output of the amplifier 163 is nominated a "control" pulse and is applied to the succeeding circuit.

In this embodiment of the invention the signal evaluating criteria are, in part, those utilized in applicant's prior pending application Ser. No. 540,973, filed Jan. 14, 1975, entitled demand Heart Pacer with Improved Interference Discrimination. Namely, any signal occurring later than a first predetermined time interval but earlier than a second predetermined time interval, measured from the preceding signal is classified as interference. These two signals may be separate sensed pulses or they may represent the start and finish of a long single pulse, differentiated by the amplifier 27. Alternatively, they may be the first pulse and a succeeding pulse of a burst of interference pulses. It simply requires that the effect is two control pulses at the output of amplifier 163 falling within the prestated temporal criteria. However, as stated above in discussion with the block diagram of FIG. 1, the precise criteria employed in signal evaluation does not effect the essence of the invention here described.

In this embodiment of the invention the first predetermined time period is chosen as 51.25 milliseconds and the second predetermined time period as 205 milliseconds, both periods being practical for the intended purpose and derivable from the binary counter 53.

NOR gates 169 and 171, and NAND gate 173 perform the time decoding functions. This function is illustrated particularly in FIG. 4. The wave form A is that seen at the terminal 95 of the counter 53 and the wave form B is that seen at the terminal 93. By combining both of these using a NOR function, a logic level 1 pulse is seen at the output of NOR gate 171 whenever both inputs are at logic level 0. The output of gate 171 is shown by wave form C in FIG. 4, a logic level 1 pulse of 205 milliseconds duration commencing at the beginning of the 820 millisecond timing cycle.

Figure 4:
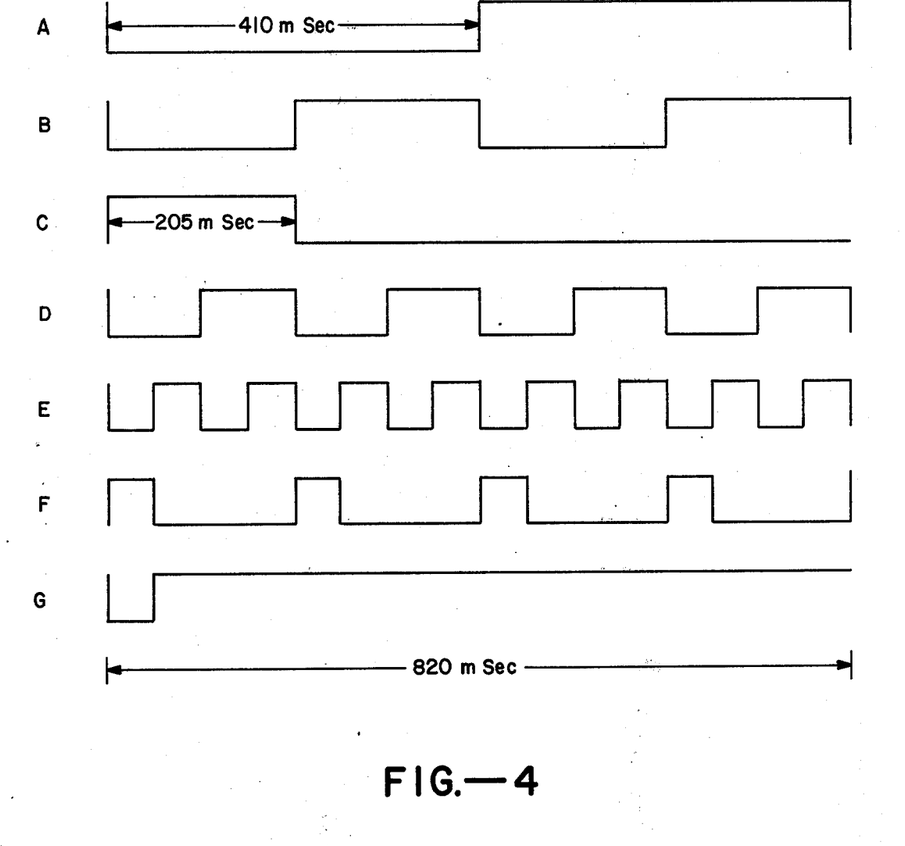
FIG. 4 is a timing chart showing the function of certain portions of the circuit shown in FIG. 3.

The wave form D of FIG. 4 is that seen at the terminal 91 of counter 53 while that seen at terminal 89 is shown as wave form E. Combining wave forms D and E, such as by the NOR gate 169, yields an output wave form as illustrated at F in FIG. 4. If the two outputs of gates 169 and 171 are combined by the NAND gate 173, that is, if the wave forms C and F of FIG. 4 are combined with the NAND function, the resultant output from the gate 173 is as illustrated as wave form G of FIG. 4, that is, a 51.25 millisecond logic level 0 pulse commencing at the start of the 820 millisecond timing cycle.

The 51.25 millisecond pulse from the gate 173 is applied to one input of NAND gate 175. Control pulses from the amplifier 163 are applied as the other input to NAND gate 175. The NAND function provides that control pulses may only appear at the output of gate 175 after the expiration of the 51.25 millisecond period measured from the reset binary counter 53.

The output control pulses from the gate 175 are inverted by gate 177 to provide correct logic levels for succeeding circuits.

The 205 millisecond logic level 1 pulse at the output of gate 171 is also applied as one input to the NAND of gate 179. Control pulses from the gate 177 are also applied as an input to the gate 179. The NAND function of gate 179 provides that pulses will appear at its output if control pulses appear at the output of gate 177 during the 205 millisecond timing period. These pulses at the output of gate 179 are designated invalidate pulses.

Thus the signal evaluation circuit provides that:
a. Any pulse occurring during the 51.25 millisecond initial period of binary counter 53 (reset by the preceding pulse), is rejected and not passed on as a control pulse to subsequent circuitry.
b. Any pulse occurring later than the 51.25 millisecond timing period, but earlier than the expiration of the 205 millisecond timing period causes both a control pulse and an invalidate pulse to be fed to the subsequent circuitry.
c. Any pulse occurring later than the 205 millisecond timing period causes only a control pulse to be fed to later circuitry.

In the circuit of FIG. 3 two bistable latches are employed. The first including NAND gates 181 and 183 and the second including NAND GATES 185 and 187. One input of gate 185 is normally held at logic level 1 by connection to the positive terminal of battery 49 through the resistor 189. Likewise, one input of gate 187 is normally held at logic level 1 by connection to the positive terminal of battery 49 through resistor 191.

Whenever a pacing pulse of logic level 0 appears at the junction 117 the pulse is applied by way of diode 193 to the input of gate 185. This pulse sets the latch including gates 185 and 187 to the state in which the output of gate 185 is at logic level 1. This logic level 1 is applied to one input of NAND gate 195 whose other input is normally held at logic level 0 by connection to ground through the resistor 197. Thus, with different logic level inputs at the gate 195 its output is at logic level 1.

The output from the gate 195 is applied as one input to the gate 183 which, combined with the gate 181, forms the first mentioned bistable latch. One input of the gate 181 is normally held at logic level 1 by connection to the positive terminal of battery 49 through resistor 199. Whenever a pacing pulse of logic level 0 appears at the junction 117 it is applied through diode 201 to that same input of gate 181 so that this bistable latch is set in the state where the output of gate 181 is at logic level 1. This logic level 1 state is applied as an input to the gate 109 to enable that gate. Thus, following any heart pacing pulse, gate 109 is enabled.

A control pulse at logic level 1 appearing at the output of inverter 177 is applied through a resistor 203 and diode 205 to the resetting input terminal 61 of counter 53. The counter 53 will thus commence a new timing cycle. The junction of the resistor 203 and diode 205 is returned to ground through a capacitor 207 so as to provide a small delay of approximately 1 microsecond between the onset of the control pulse at the output of the inverter 177 and the instant the counter 53 is reset. Without this small delay the leading edge of a pulse at the output of the inverter 177 will immediately reset the counter 53 thus immediately disabling gate 175. As a consequence the width of the pulse at the output of the gate 177 would be chopped to an extremely small duration and insufficient to reliably operate other functions responsive to the control pulse.

The control pulse from the inverter 177 which resets the timing cycle of the counter 53 is also applied through diode 209 as an input to the gate 195 whose other input is, as earlier stated, at logic level 1. With both inputs of the gate 195 being at logic level 1, a logic level 0 output pulse is provided which is applied as an input to the gate 183 unsetting the latch comprising gates 181 and 183. The state of the output of gate 181 is thus reversed from logic level 1 to logic level 0 thereby disabling gate 109. With gate 109 disabled, the counter 55 can conclude its timing cycle without causing the pacing pulse to be applied to the heart.

Thus, a control pulse in response to a valid heartbeat signal resets the timing cycle of the counter 53 and disables the output of the counter 55. In the absence of any further control pulses in response to a valid heartbeat signal, the counter 53 will run out to the completion of its timing period causing the delivery of a heartbeat stimulating impulse. Simultaneously, the counter 55 is reset, the latch including gates 181 and 183 is reset and the gate 109 is reenabled.

As described earlier, an invalidate pulse will always be coincident with the control pulse when using the signal evaluation circuit of this embodiment, but need not necessarily be so within the essence of the invention.

In this embodiment of the invention, in order that an invalidate pulse be generated, it is necessary that a preceding control pulse had been generated with a separation of greater than 51.25 milliseconds, but less than 205 milliseconds between each. The first occurring pulse is tentatively accepted as representing a valid heartbeat signal. The timing cycle of the counter 53 is reset and the latch comprising gates 181 and 183 is unset so as to disable the gate 109. When the logic level 0 invalidate pulse occurs at the output of the gate 179 it is coupled by way of diode 211 to reset the bistable latch comprising gates 181 and 183. The gate 109 is therefore, reenabled. Simultaneously, the invalidate pulse is coupled by diode 213 to unset the second latch comprising gates 185 and 187 and thereby disable the gate 195. Note that because of the microsecond delay of the control pulse produced by resistor 203 and capacitor 207, ad the submicrosecond operating speed of the logic gates, the gate 195 is unset before the arrival of the control pulse and thus there is no competition for control of the latch comprising gates 181 and 183. With the second latch, comprising gates 185 and 187, unset and gate 195 disabled, no further control pulses can unset the latch comprising gates 181 and 183. The counter 55 thus runs out to produce a pacing pulse to the heart with simultaneous reset of the counter 53, as well as reset of the latch comprising gates 185 and 187.

In terms of the demonstrable function of the pacer, this means that a signal sensed by the amplifier 141 at, say 400 milliseconds after a base rate pacing beat, will reset the counter 53 and disable the gate 109. A further signal sensed at sometime between 51.25 and 205 milliseconds later reenables the output of counter 55 which stays enabled until it has produced its next pacing pulse. At that time the total cycle reverts to the start condition.

For the patient this is a totally safe mode of operation since a single sensed interference pulse shuts down the demand function until the next pacing pulse has been delivered to the patient. However, a later sensed signal prior to the completion of the timing cycle of the counter 55 may well be valid.

As stated earlier in the description of the latching functions related to FIG. 1, it is possible to structure the latching function so that after the receipt of an invalidate pulse, a later sensed tentatively valid signal resets the counter 53 and disables the output of counter 55. This allows an ongoing situation of acceptance or reversal of any tentative decision.

The illustrative embodiment of the invention shown in FIG. 3, may be simply modified to allow the alternative mode of latch function shown in FIG. 1. All that is required is that gates 185 and 187, resistors 189 and 191, and diodes 193 and 213 be deleted. The upper input of gate 195 is connected directly to the output of gate 179. Diode 209 is connected directly to the output of the inverter 177 rather than to the junction of the resistor 203 and capacitor 207. Depending upon the working speed of the logic technology employed, it may be found necessary to add a resistive capacitive time delay similar to resistor 203 and capacitor 207 between the output of the gate 195 and the input of gate 183. With this minor rearrangement it is seen that the latch comprising gates 181 and 183 may be reset and the gate 109 disabled by any control pulse while a coincident control pulse and invalidate pulse will always set the latch comprising gates 181 and 183 to enable the gate 109.

As stated earlier, the choice between the two alternative latching configurations is essentially dictated by the type of signal evaluation circuit employed and the objective judgment of the individual designer seeking to maximize the explotation of the invention. The invention described is but a particular preferred embodiment which serves to illustrate the manner of practical application of the essence of the invention. Numerous rearrangements and modifications may be devised without departing from the essence of the invention.

Referring specifically to the circuit component of FIG. 3, the battery 49 comprises three RMI mercury cells. The counters 53 and 55 are each binary dividers type MC14040Cp, manufactured by Motorola Semiconductors, Inc. The amplifiers 141 and 163 are monolithic operational amplifiers type uA776 (U5B7776393) manufactured by Fairchild Semiconductor of Mountain View, California. All of the NAND gates are one quarter of the type MC14011AL (C.MOS) quad NAND gate. Each of the NOR gates is one quarter of the type MC14001AL (C.MOS) quad NOR gate. The gates are manufactured by Motorola Semiconductors, Inc. of Phoenix, Arizona. Each of the transistors 57, 59 and 125 is of the type BC109. Each of the diodes is a type 1N914. The values of the resistors and capacitors are as set forth in the table below:

| Resistors | |
| --- | --- |
| 65 | 1.0M |
| 67 | 24.0M ohm |
| 69 | 24.0M ohm |
| 71 | 1.0M ohm |
| 103 | 1.0M ohm |
| 119 | 1.0M ohm |
| 123 | 33K ohm |
| 143 | 15 M ohm |
| 145 | 2.2 M ohm |
| 147 | 180 K ohm |
| 149 | 4.7 M ohm |
| 151 | 1.5 M ohm |
| 155 | 2.7M ohm |
| 157 | 15 K ohm |
| 165 | 10 K ohm |
| 167 | 68 OK ohm |
| 189 | 1.0 M ohm |
| 191 | 100 K ohm |
| 197 | 1.0 M ohm |
| 199 | 1.0 M ohm |
| 203 | 10K ohm |
| 215 | 27 K ohm |
| 219 | 1.0 M ohm |

| Capacitors | |
| --- | --- |
| 73 | 22pF |
| 75 | 22pF |
| 127 | 15uF |
| 139 | 0.22uF |
| 153 | 10 uF |
| 159 | 0.22 uF |
| 161 | 0.0022uF |
| 207 | 0.001uFd |
| 217 | 33uF |

What is claimed is:

1. A heart pacer comprising terminal means for electrical coupling to a patient, electrical impulse generating means connected to said terminal means for applying electrical impulses to said terminal means, said electrical impulse generating means including first and second electrical impulse timing means simultaneously generating first and second predetermined timing periods respectively, said electrical impulse generating means further including enabling means for selecting one of said electrical impulse timing means to apply electrical impulses to said terminal means at its predetermined timing period.

2. A heart pacer as defined in claim 1, wherein said terminal means includes at least one terminal for connection to the patient's heart.

3. A heart pacer as defined in claim 1, wherein the first and second predetermined timing periods are equal to each other.

4. A heart pacer as defined in claim 1, together with means coupled to said terminal means for generating control pulses responsive to signals appearing at said terminal means, said enabling means being responsive to said control pulses to select one of said electrical impulse timing means.

5. A heart pacer as defined in claim 4, wherein said terminal means includes at least one terminal for connection to the patient's heart.

6. A heart pacer comprising terminal means for electrical coupling to a patient, pulse generating means coupled to said terminal means for supplying electrical impulses to said terminal means at timed intervals, said pulse generating means including first and second pulse generating timing means having first and second predetermined normal timing periods respectively, said first and second pulse generating timing means being simultaneously operative, one of said pulse generating timing means being selective to provide a normal timed interval between successive electrical impulses applied to said terminal means, means coupled to said terminal means for generating control pulses responsive to signals appearing at said terminal means above a predetermined level, means responsive to said control pulses for setting said second pulse generating timing means to begin a new timing period earlier than its normal commencement of a new timing period and inhibit means responsive to said control pulses for inhibiting the generation by said first timing means of the next otherwise generated electrical impulse.

7. A heart pacer, as defined in claim 6, wherein said terminal means includes at least one terminal for connection to the patient's heart, said pulse generating means being coupled to said terminal for supplying electrical impulses to the heart of said patient.

8. A heart pacer as defined in claim 6, wherein said first and second predetermined normal timing periods are equal to each other.

9. A heart pacer as defined in claim 6, together with means coupled to said terminal means for generating invalidate pulses in response to noise signals above a predetermined level at said terminal means and disabling means responsive to said invalidate pulses for disabling said inhibit means.

10. A heart pacer as defined in claim 9, wherein said disabling means includes means responsive to said control pulses for reenabling said inhibit means.

11. A heart pacer as defined in claim 9, wherein the said disabling means includes means responsive to said electrical impulses for reenabling said inhibit means.

12. A heart pacer as defined in claim 9, wherein said means generating invalidate pulses includes means responsive to signals above a predetermined level appearing upon said terminal means when said signals occur within a time frame beginning at a first predetermined time period and ending at a second predetermined time period, both first and second time periods being measured from the preceding control pulse.

13. A heart pacer as defined in claim 12, wherein said first predetermined time period is greater than the time period between the first and last of control pulses derived in response to the appearance upon said terminal means of the QRS signal of a single heart beat.

14. A heart pacer as defined in claim 12, wherein said second predetermined time period is less than the time period between two natural heartbeats.

15. A heart pacer as defined in claim 6, wherein said means generating control pulses includes frequency discrimination means optimising the operation thereof by signals of frequencies representative of the heartbeat QRS signals appearing on said terminal means.

16. A heart pacer as defined in claim 6, wherein said first and second pulse generating timing means run simultaneously.

* * * * *